(12) United States Patent
Warrington et al.

(10) Patent No.: US 10,143,815 B2
(45) Date of Patent: Dec. 4, 2018

(54) PORTABLE SUCTION DEVICE

(71) Applicants: Richard Warrington, Laguna Niguel, CA (US); Erica W Stump, Laguna Niguel, CA (US)

(72) Inventors: Richard Warrington, Laguna Niguel, CA (US); Erica W Stump, Laguna Niguel, CA (US)

( * ) Notice: Subject to any disclaimer, the term of this patent is extended or adjusted under 35 U.S.C. 154(b) by 512 days.

(21) Appl. No.: 14/686,713

(22) Filed: Apr. 14, 2015

(65) Prior Publication Data
US 2015/0290411 A1 Oct. 15, 2015

Related U.S. Application Data

(60) Provisional application No. 61/979,346, filed on Apr. 14, 2014.

(51) Int. Cl.
*A61M 16/04* (2006.01)
*A61M 1/00* (2006.01)

(52) U.S. Cl.
CPC ........ *A61M 16/047* (2013.01); *A61M 1/0023* (2013.01); *A61M 16/0434* (2013.01); *A61M 2205/8206* (2013.01); *A61M 2209/10* (2013.01)

(58) Field of Classification Search
CPC .. A61M 1/0011; A61M 1/008; A61M 1/0086; A61M 16/0463; A61M 16/047; A61M 16/0816; A61M 16/0833; A61M 1/0001; A61M 1/0017; A61M 1/0023; A61M 1/0027; A61M 1/0031; A61M 1/0035; A61M 1/0037; A61M 1/0049; A61M 1/005; A61M 1/0052; A61M 1/0058; A61M 1/0066; A61M 1/0072; A61M 1/0084; A61M 1/0088; A61M 1/06; A61M 1/062; A61M 1/066; A61M 11/06; A61M 15/08; A61M 2205/075; A61M 2205/12; A61M 2205/123; A61M 2205/128; A61M 2205/215; A61M 2205/3382; A61M 2205/50; A61M 2205/587; A61M 2205/7536; A61M 2205/8206; A61M 2210/0618; A61M 2210/0662;
(Continued)

(56) References Cited

U.S. PATENT DOCUMENTS

| 3,735,751 A | * | 5/1973 | Katz | A61B 1/0055 600/563 |
| 3,794,026 A | * | 2/1974 | Jacobs | A61M 16/00 128/200.13 |

(Continued)

*Primary Examiner* — Annette Dixon
(74) *Attorney, Agent, or Firm* — Allen F. Bennett; Bennett Intellectual Property

(57) ABSTRACT

A portable suction device is rechargeable, lightweight, and compatible with disposable medical catheters. The unit can be operated with one hand, while a user may attend to the patient with the other hand. The suction device may feed into a sterile collection vessel, which can be replaceable, cleanable and/or reusable. A rechargeable battery pack for power may be located in the base of the unit. A vacuum pump may supply negative air flow to draw fluids out of a patient. An inline one-way filter located between the catheter and the vessel may prevent bacteria and other possible contaminants from traveling up-line to the patient. The unit may be designed specifically for use by tracheotomy patients and their caregivers.

17 Claims, 2 Drawing Sheets

(58) Field of Classification Search
CPC . A61M 27/00; A61M 3/0283; A61B 10/0283; A61G 2203/46; A61G 9/006; A61H 35/04; F04B 45/041
USPC ............ 128/200.13, 202.22, 204.26, 207.14, 128/207.15; 604/30, 31, 317, 319, 322, 604/326, 503, 67, 97.02
See application file for complete search history.

(56) References Cited

U.S. PATENT DOCUMENTS

| | | | | |
|---|---|---|---|---|
| 4,710,165 A * | 12/1987 | McNeil | ............... | A61M 1/0023 604/31 |
| 5,776,119 A * | 7/1998 | Bilbo | .................. | A61M 1/0023 604/317 |
| 5,819,723 A * | 10/1998 | Joseph | ................ | A61M 16/044 128/202.22 |
| 2003/0195482 A1* | 10/2003 | Schultz | ............... | A61M 1/0047 604/317 |
| 2011/0060300 A1* | 3/2011 | Weig | ....................... | A61F 5/451 604/319 |

\* cited by examiner

PORTABLE SUCTION DEVICE

CROSS-REFERENCE TO RELATED APPLICATIONS

This application claims priority to U.S. Provisional Application Ser. No. 61/979,346 filed on Apr. 14, 2014, the contents of which are hereby incorporated by reference in their entirety.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

STATEMENT REGARDING FEDERALLY SPONSORED RESEARCH OR DEVELOPMENT

Not Applicable.

BACKGROUND OF THE INVENTION

Field of Endeavor

This invention relates, in general, to a portable suction device and in particular, to a portable suction device which can be used with one hand, is powered by rechargeable batteries, and contains a removable, replaceable collection vessel connected by tubing to a user handle.

Background Information

In a variety of situations, persons are sent home from the hospital with medical conditions that require medical devices. As a result, more and more medical devices are being adapted for use by nonmedical professionals outside of a hospital or in a carefully controlled environment.

Is has become more and more common for persons to leave a hospital with an open tracheotomy. The tracheotomy must be maintained in a variety of ways, including suctioning out mucus and other fluids from the lungs and bronchial tubes.

Often the person having the tracheotomy is incapable of performing this suction and cleaning procedure themselves. Thus, a caregiver is required to apply suction to the tracheotomy. Because clearing the tracheotomy is often a traumatic experience for a patient, the caregiver must not only perform the required maintenance, but must also control the patient.

Common suction pumps, while effective, are often bulky and difficult to manipulate. Often, they require use of both hands. This may be particularly impractical when the patient is very young, very old or not cooperative.

In view of the foregoing, there is a need for a suction device for use with tracheotomies and other situations that requires use of a suction pump which is small, compact and operable with only a single hand. It is therefore desirable to provide an easy to use, effective suction device that may be reliably and accurately used with only one hand.

BRIEF SUMMARY OF THE INVENTION

Accordingly, the primary object of the present invention is to provide a portable battery powered suction device which uses a vacuum suction unit mounted within an ergonomic base, circular in shape, and made of tubing.

In one embodiment, the internal parts are designed to be fitted within the base of the unit. A disposable off-the-shelf catheter is used in the tubing to direct secretions to the vessel within the base of the unit. Inside the base of the portable suction device is a vessel made of disposable plastic for the collection of secretions. This vessel is connected to the pump via plastic tubing. The vessel is also connected to the handle portion of the suction device by tubing to direct secretions collected via a disposable catheter. The handle portion is also the cover to the base and provides a cover for the internal parts. A two position pressure switch is located on the handle. This switch allows for the suction device to be turned on and off with one push of the button on the switch, or kept on via pressure, and turns off upon release of said pressure. The base of the unit is designed to hold the secretions vessel, the pump, and the rechargeable battery. The present invention is significantly different than previous prior art devices in that the unit can be used single-handedly by the user, can use already available medical supplies in the form of a disposable catheter, uses a two-stage switch for temporary or long-term operation, and can be assembled using either custom manufactured or off-the-shelf parts. The invention is less cumbersome, smaller, and more lightweight than currently available portable suction units. It is an object of the present invention to provide an easily constructed portable suction unit which is economical to produce and manufacture, and economical for the end user to buy. It is the object of the portable suction device to be easier to use than currently available units since the user can operate the portable suction device with one hand while attending to the patient with the other. These and other objects and advantages of the present invention will be fully apparent when the description and drawings are taken into consideration.

In one embodiment, a portable suction device held and operated using a single hand for use cleaning a tracheostomy tube comprises a body sized to be held by a single hand, a base attached to a bottom of the body, a projection having a distal anchor point, a source of electrical power, a suction pump, a collection canister in fluid communication with the suction pump, a power button positioned on the device such that it is readily accessible to one or more digits of the single hand holding the device, a suction inlet accessible from outside the body and in fluid communication with the collection canister, a suction catheter having a proximal end removably attached to the suction inlet, a filter between the suction catheter and the collection canister, and a suction valve having a trigger positioned on the device such that it is readily accessible to one or more digits of the single hand holding the body.

The power source is a battery located in the base and the device has a low center of gravity. The power button is a two-stage on/off switch for providing power to the suction pump and the suction valve modulates the amount of suction supplied to the suction catheter. The body is substantially cylindrical and the power button is accessible to the index finger of the hand holding the device and the suction valve trigger is accessible to the thumb of the hand holding the device.

The anchor point is an annular cuff that abuts a tracheostomy tube. The distal end of the suction catheter extends from the annular cuff a distance that is less than the length of the tracheostomy tube. The suction pump and the collection canister are housed within the body of the device.

The portable suction device also may include an air pressure detector that actuates an alarm when it detects that the suction applied to the suction catheter drops below a predetermined amount. The portable suction device may also include a graduated window for viewing the amount of material collected within the collection canister. The power source may be a battery located in the base and the device has a low center of gravity and the power button is a two-stage on/off switch for providing power to the suction pump and the suction valve modulates the amount of suction supplied to the suction catheter.

In one embodiment, the body is substantially cylindrical; the power button is accessible to the index finger of the hand holding the device and the suction valve trigger is accessible to the thumb of the hand holding the device and the anchor point further comprises and annular cuff that abuts a tracheostomy tube. The suction catheter extends from the annular cuff a distance that is less than the length of the tracheostomy tube. The suction pump and the collection canister are housed within the body of the device.

In one embodiment, a portable suction device is held by a single hand for use in removing fluids from a stoma. The device includes a collection canister, a suction pump in fluid communication with the collection canister, a suction inlet port in fluid communication with the collection canister, a filter positioned between the suction inlet port and the collection canister, a projection having a distal anchor point, a suction catheter having a proximal end removably attached to the suction inlet and a distal end removably attached to the distal anchor point, and a power switch is actuated by one or more digits of the single hand holding the device and modulating the amount of suction applied by the suction pump to the collection canister.

The portable suction includes an anchor point having an annular cuff that abuts a tracheostomy tube, and wherein the suction catheter extends from the annular cuff a distance that is less than the length of the tracheostomy tube. The suction pump and the collection canister are housed within the body of the device. An air pressure detector actuates an alarm when it detects that the suction applied to the suction catheter drops below a predetermined amount. The body includes a graduated window for viewing the amount of material collected within the collection canister.

In one embodiment, the portable suction device includes an air pressure detector that actuates an alarm when it detects that the suction applied to the suction catheter drops below a predetermined amount and the anchor point has an annular cuff that abuts a tracheostomy tube. The suction catheter extends from the annular cuff a distance that is less than the length of the tracheostomy tube. The suction pump and the collection canister are housed within the body of the device.

In another embodiment, a one-handed method for cleaning a tracheostomy tube includes providing a hand held suction device comprising a body sized to fit within the grip of a single adult hand and housing a collection canister, a suction pump in fluid communication with the collection canister and a power source. A suction catheter is attached to an inlet providing fluid communication with the collection canister. The suction catheter is affixed to an annular cuff located at a distal end of a projection that extends from the body of suction device. The distal end of the suction catheter extends a distance from the annular cuff that is less than a length of a tracheostomy tube. Power is supplied by the power source to the suction pump by actuating a power button accessible by one or more digits of a hand holding the suction device. The distal end of the suction catheter is inserted into the tracheostomy tube, thereby suctioning material out of the tracheostomy tube and into the collection canister.

The method may also include modulating the amount of suction supplied to the suction catheter by manipulating a suction valve operable by one or more digits of the single adult hand holding the suction device. The method may also include monitoring the amount of material collected in the collection canister by viewing the material through a window on the suction device. The power source is a battery housed in the body of the suction device.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
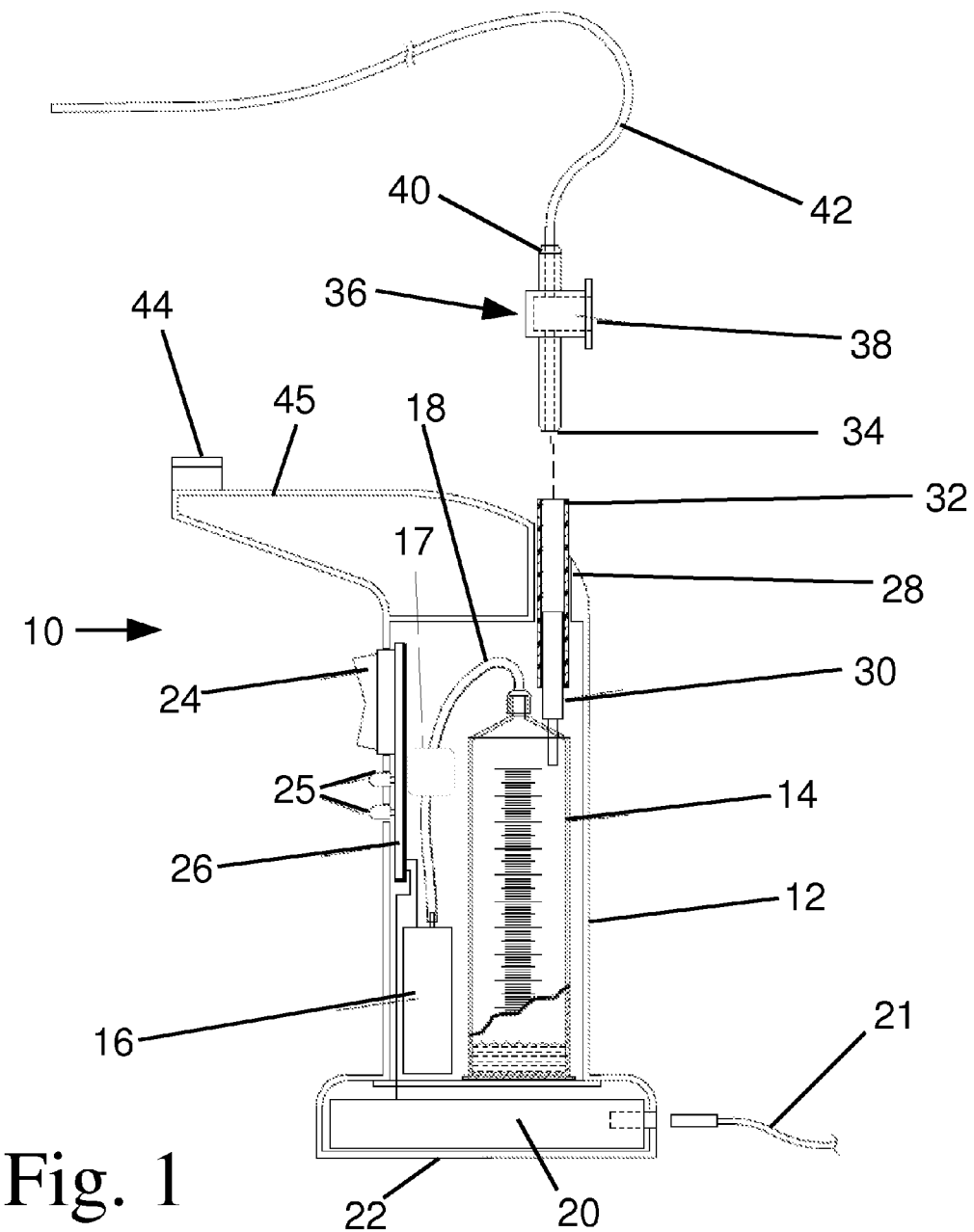
FIG. 1 is a cut-away view of a suction device in accordance with the principles of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Disclosed is a portable, rechargeable, lightweight, medically compatible suction device, for use with disposable medical catheters. The unit may be operated with one hand, while a user may attend to the patient with the other hand. An on/off switch for operating the internal pump may include two functionalities. One function may include the pump being on so long as the switch is activated. The other function may turn the pump on when pressure is applied to the switch, and off when pressure is released.

The suction device may feed into a sterile collection vessel, which can be either replaceable, or cleanable and reusable. Commonly available medical suction catheters may be used to suction secretions or fluids from the patient and be disposed of. A rechargeable battery pack for power may be located in the base of the unit. A vacuum pump may be located in the base, and may apply vacuum pressure such that secretions may be drawn out of the patient, through the disposable catheter, and into the vessel. An inline one-way filter located between the catheter and the vessel may prevent bacteria and other possible contaminants from traveling up-line to the patient. The unit may be designed specifically for use by tracheotomy patients and their caregivers.

In greater detail, the hand-held, battery operated suction device allows a single user to apply suction into a tracheotomy or other opening. The suction device may have a compact body easily held in one hand, with an internal pump and reservoir. The reservoir may be able to accommodate about 100 ml of fluid, be removable, be cleanable, and be replaceable.

The suction device may include a rechargeable battery, similar to modern tool designs such as drills, flashlights, etc. A finger operated trigger may be used as an on-off switch.

The pump may be capable of producing a sustained 80-400 mmHg negative air pressure for up to 30 seconds. A rechargeable lithium battery pack may provide about 24 hours of on-off use before needing recharging.

The suction device may be adapted for use with currently available disposable silicone suction catheters. A user may control the suction applied by the device by actuating the trigger with the user's thumb, turning the pump on or off as desired. By allowing a user to actuate the pumping mechanism using the thumb of the hand holding the suction device, the user's other hand is free for manipulating the patient and the catheter.

FIG. 1 shows portable suction device 10 in accordance with the principles of the invention. The portable suction device 10 is contained within body 12. The body may be sized to fit comfortably with the grip of one hand of an adult. In this embodiment, the body 12 is substantially cylindrical. A base 22 may be attached to the bottom of the body 12 and may be wider than the body in order to allow it to rest stably on a flat surface. A projection 45 may extend from the top of the body 12 opposite the base, or alternatively from another location on the body 12. A collection canister 14 may be removably secured within the body 12 or may optionally be an integral component of the body 12. A suction pump 16 may provide negative pressure, i.e. suction, to the collection canister 14 through a tube 18. The suction pump 16 may be powered by a power source 20 located in the base 22 at the bottom of the body 12. The power source may be a battery. The base 22 may have a flat, planar bottom surface such that the portable suction device 10 may be placed in an upright position as shown in FIG. 1. It may be desirable to locate a power source 20, for example a battery, in the base, thereby lowering the center of gravity and thus improve stability of the portable suction device 10 when not in use.

The power source 20 may be a rechargeable battery that may be recharged by connection to charging cord 21. A circuit board 26 may support a switch 24 that may regulate the application of power to suction pump 16 from power source 20. Circuit board 26 may also be in communication with indicator lights 25, which may serve to indicate the amount of charge available from the power source 20, whether the unit is turned on, or other information. The switch 24 may be a simple two-stage on/off switch or may alternately be a switch that allows modulation of the amount of power supplied to the pump, thereby modulating the amount of suction applied to the collection canister 14.

Collection canister 14 may also be in fluid communication with a suction inlet 32 by means of a conduit housing a filter 30. The suction inlet 32 may be adapted to removably attach to connector 34 extending from a suction valve 36 at suction inlet 32. Suction valve 36 may be include a trigger 38 that may be actuated by a digit, for example a finger or thumb, of the hand holding the portable suction device 10. The suction valve 36 may be closed when the trigger 38 is depressed and opened when the trigger is disengaged by the operator's digit. A suction catheter 42 may removably connect to the valve at a connection mechanism 40. The body 12 of the portable suction device 10 may optionally include an anchor point 44 on distal end of the projection 45 that may removably attach to the suction catheter and allow a user to accurately and precisely place the catheter and apply suction in a fixed, steady position without using a second hand to position and manipulate the suction catheter. The portable suction device 10 may also optionally include a flowmeter 17 which may also include a pressure gauge and may detect when airflow or air pressure/suction rise above or below a preferred range. The flowmeter 17 may activate one or more indicator lights 25 or emit an audio alarm when the flow or pressure departs from the preferred range.

In use, an operator may grasp with one hand the portable suction device 10 about the body 12. The body 12 may optionally have a surface designed to allow the portable suction device 10 to be firmly gripped by the user. For example, the body 12 may have a rubber coating, a knurled surface or have channels and ridges to accommodate the fingers and thumb of a human hand. Optionally, the body 12 may simply be substantially cylindrical, or have an elliptical cross-section.

When the portable suction device 10 is held in one hand, a digit such as for example the index may manipulate the switch 24 in order to turn on or off the portable suction device 10. When actuated, the suction pump 16 may provide suction, or negative pressure, to collection canister 14. When the suction valve 36 and a suction catheter 42 are engaged with connecting tube 28 by means of suction inlet 32, fluids may be sucked through the suction catheter 42, through filter 30 and collected in collection canister 14. The placement of connecting tube 28 and tube 18 may prevent fluids from entering tube 18 and damaging suction pump 16. The filter 30 may optionally be a check valve preventing flow of material from the collection canister 14 back into the suction catheter 42.

By depressing the trigger 38, using for example the thumb of the hand holding the portable suction device 10, a user may modulate the amount of suction applied to suction catheter 42. This may allow for "fine-tuning" of the amount of suction applied by suction catheter 42 to a tracheostomy or other stoma or opening. By attaching the suction catheter 42 to anchor point 44, the user position and manipulate the placement of the suction catheter using the same hand that holds the portable suction device 10. By adjusting the length the suction catheter 42 extends from the anchor point, the portable suction device 10 may insure that the suction catheter 42 is not inserted beyond a preferred depth within a tracheostomy or other stoma.

Figure 2:
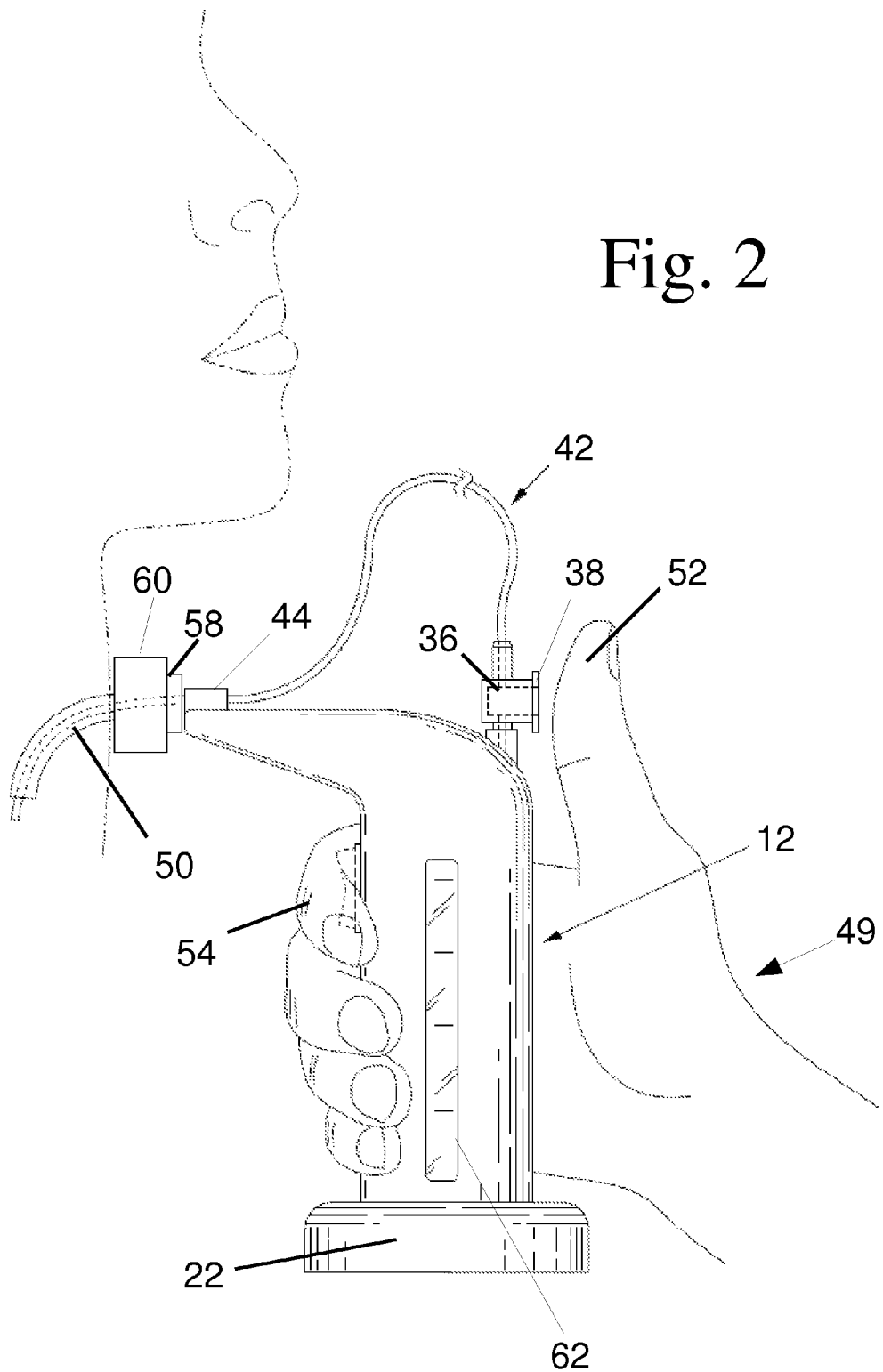
FIG. 2 is a perspective, environmental view of a suction device in accordance with the principles of the invention.

FIG. 2 shows the portable suction device 10 in use. An operator grasps the body 12 with a single hand 49. The user may actuate the switch 24 using an index finger 54 of single hand 49, activating the suction pump and thereby applying suction to the suction catheter 42. An operator may modulate the amount of suction applied to the suction catheter 42 by impinging the trigger 38 of the valve 36 using a thumb 52 of single hand 49. An annular cuff 58 at anchor point 44 attaches to the suction catheter 42. The suction catheter may be extended a desired distance from the annular cuff 58, and that distance is maintained by the secure grip of the annular cuff 58. The suction catheter 42 may be inserted into a tracheostomy tube 50 until the annular cuff 58 abuts the catheter tube entrance 60. This may allow the operator to very accurately and precisely control the suction applied to the tracheostomy tube 50 and the depth to which a suction catheter 42 may be inserted using only a single hand 49. As a result, the operator's other hand is free to cradle a person's head, manage the patient or another object, or perform other functions, while simultaneously using the portable suction device 10.

The device may also include a window 62 allowing an operator to view the material within the collection canister. The window 62 may optionally be graduated. That is, the window 62 may include lines, notches or other markers indicating volume within the collection canister. Thus, the operator may be able to measure the amount of fluid or other material collected while cleaning a catheter tube, stoma or other object. The flowmeter 17, by actuating lights or an audio signal, may alert the operator that the flow or suction has risen above or dropped below a desired range. This may indicate that air flow has been blocked by a clog somewhere in the system, or may indicate that there is no more material to be drawn out of a tracheostomy tube and that cleaning is complete.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A portable suction device for use cleaning a tracheostomy tube comprising:
   a body sized to be held by a single hand;
   a base attached to a bottom of the body;
   a projection having a distal anchor point;
   a source of electrical power;
   a suction pump;
   a collection canister in fluid communication with the suction pump;
   a power switch positioned on the device;
   a suction inlet accessible from outside the body and in fluid communication with the collection canister;
   a suction catheter having a proximal end removably attached to the suction inlet;
   a filter between the suction catheter and the collection canister; and,
   a suction valve having a trigger positioned on the device wherein the anchor point further comprises an annular cuff that abuts the tracheostomy tube entrance, and wherein a distal end of the suction catheter extends from the annular cuff a distance that is less than the length of the tracheostomy tube.

2. The portable suction device of claim 1 wherein the source of electrical power is a battery located in the base.

3. The portable suction device of claim 1 wherein the power switch is a two-stage on/off switch for providing power to the suction pump and the suction valve modulates the amount of suction supplied to the suction catheter.

4. The portable suction device of claim 1 wherein the body is substantially cylindrical.

5. The portable suction device of claim 1 wherein the suction pump and the collection canister are housed within the body of the device.

6. The portable suction device of claim 1 further comprising a flowmeter that detects that the suction provided by the suction pump drops below or rises above a predetermined range.

7. The portable suction device of claim 1 wherein the body further includes a graduated window for viewing the amount of material collected within the collection canister.

8. The portable suction device of claim 7 wherein:
   the power source is a battery located in the base;
   the power switch is a two-stage on/off switch for providing power to the suction pump and the suction valve modulates the amount of suction supplied to the suction catheter
   the body is substantially cylindrical;
   and
   the suction pump and the collection canister are housed within the body of the device.

9. A portable suction device held by a single hand for use in removing fluids from a tracheostomy tube comprising:
   a collection canister;
   a suction pump in fluid communication with the collection canister;
   a suction inlet port in fluid communication with the collection canister;
   a filter positioned between the suction inlet port and the collection canister;
   a projection having a distal anchor point;
   a suction catheter having a proximal end removably attached to the suction inlet port and a distal end removably attached to the distal anchor point; and,
   a power switch modulating the amount of suction applied by the suction pump to the collection canister;
   wherein the anchor point further comprises and annular cuff that abuts the tracheostomy tube, and wherein the suction catheter extends from the annular cuff a distance that is less than the length of the tracheostomy tube.

10. The portable suction device of claim 9 wherein the suction pump and the collection canister are housed within the body of the device.

11. The portable suction device of claim 9 further comprising a pressure gauge that actuates an audio signal when it detects that the suction applied to the suction catheter drops below or rises above a predetermined amount.

12. The portable suction device of claim 9 wherein the body further includes a graduated window for viewing the amount of material collected within the collection canister.

13. The portable suction device of claim 12 further comprising a flowmeter that detects when the suction applied to the suction catheter drops below or rises above a predetermined amount; and wherein the suction pump and the collection canister are housed within the body of the device.

14. A one-handed method for cleaning a tracheostomy tube comprising:
    providing a hand held suction device comprising a body housing a collection canister, a suction pump in fluid communication with the collection canister and a power source;
    attaching a suction catheter to an inlet providing fluid communication with the collection canister;
    affixing the suction catheter to an annular cuff located at a distal end of a projection that extends from the body of suction device such that the distal end of the suction catheter extends a distance from the annular cuff that is less than a length of the tracheostomy tube;
    supplying power from the power source to the suction pump by actuating a power switch accessible by one or more digits of a hand holding the suction device;
    inserting the distal end of the suction catheter into the tracheostomy tube, thereby suctioning material out of the tracheostomy tube and into the collection canister.

15. The method of claim 14 further comprising modulating the amount of suction supplied to the suction catheter by manipulating a suction valve operable by one or more digits of the single hand holding the suction device.

16. The method claim 15 further comprising monitoring the amount of material collected in the collection canister by viewing the material through a window on the suction device.

17. The method of claim 16 wherein the power source is a battery housed in the body of the suction device.

\* \* \* \* \*